United States Patent [19]
Grasselli et al.

[11] 3,956,378
[45] May 11, 1976

[54] PROCESS FOR THE MANUFACTURE OF UNSATURATED ALDEHYDES AND ACIDS FROM THE CORRESPONDING OLEFINS

[75] Inventors: Robert K. Grasselli, Chagrin Falls; Dev D. Suresh, Macedonia; Ernest C. Milberger, Solon, all of Ohio

[73] Assignee: The Standard Oil Company (Ohio), Cleveland, Ohio

[22] Filed: Aug. 20, 1973

[21] Appl. No.: 390,094

Related U.S. Application Data

[62] Division of Ser. No. 224,967, Feb. 9, 1972, Pat. No. 3,892,794.

[52] U.S. Cl. .......................... 260/533 N; 260/604 R
[51] Int. Cl.² ........................................... C07C 51/32
[58] Field of Search .................... 260/533 N, 604 R

[56] References Cited
UNITED STATES PATENTS

| | | | |
|---|---|---|---|
| 3,468,958 | 9/1969 | Callahan | 260/533 N |
| 3,551,470 | 12/1970 | Shaw et al. | 260/533 N |
| 3,625,867 | 12/1971 | Yoshino et al. | 260/465.3 |

*Primary Examiner*—James A. Patten
*Assistant Examiner*—Paul J. Killos
*Attorney, Agent, or Firm*—Herbert D. Knudsen

[57] ABSTRACT

A process for the catalytic oxidation of olefins to unsaturated aldehydes and acids and the ammoxidation of olefins to unsaturated nitriles in which the catalyst comprises a promoted, reduced, antimony oxide-molybdenum oxide-containing catalyst.

3 Claims, No Drawings

PROCESS FOR THE MANUFACTURE OF UNSATURATED ALDEHYDES AND ACIDS FROM THE CORRESPONDING OLEFINS

This is a division of application Ser. No. 224,967, filed Feb. 9, 1972, now U.S. Pat. No. 3,892,794.

This invention relates to a process for the catalytic oxidation of olefins to unsaturated aldehydes and acids and to the oxidation of olefin-ammonia mixtures to unsaturated nitriles. More specifically this invention relates to a process for the catalytic oxidation of olefins such as propylene and isobutylene to acrolein, acrylic acid, methacrolein, and methacrylic acid, respectively, and the ammoxidation of propylene and isobutylene, respectively, to acrylonitrile and methacrylonitrile.

The catalyst of this invention is composed of the oxides of molybdenum and antimony and preferably contains other metal oxides. The catalyst compositions most useful in this invention are represented by the following formula:

$$A_a B_b Sb_c Mo_d O_e$$

wherein A comprises one or more of the promoting elements selected from the group consisting of tellurium, tungsten, titanium, manganese, nickel, iron, copper, lead, rhenium, bismuth, tin, uranium, chromium, phosphorus and boron, and B is a member selected from the group consisting of molybdenum, tungsten, aluminum, nickel and sulfur, and wherein $a$ is a number of from 0.001 to 1.0, $b$ is a number of from 0 to 2.0, $c$ is a number from 1 to 9, $d$ is a number from 1 to 9, and $e$ is a number dependent upon the valence requirements of the combined metals. The preferred catalysts include those compositions wherein $a$ is 0.005 to 0.5, $b$ is 0.001 to 1.0, $c$ is 1 to 8, $d$ is 1 to 8 and $e$ is 4 to 40.

The method employed in preparing the catalyst of this invention is critical to the oxidation process described herein. In the empirical formula designating the composition of the catalyst of this invention, A in the formula represents a promoter element and B represents a reducing element. The method employed in preparing the catalyst departs from the usual classical procedures involving co-precipitation or impregnation techniques and involves the simple mixing of the respective metal oxides of antimony and molybdenum, the reducing agent and the compound of the promoter element or elements as a slurry in water.

In a preferred procedure for combining the essential elements of the catalyst composition, an aqueous suspension of molybdenum trioxide is pre-reduced in a controlled manner so that at least some of the molybdenum is reduced to a valence state below +6 before the molybdenum oxide is mixed with a lower oxide of antimony, antimony trioxide. A wide range of reducing agents can be employed for this purpose including finely divided or colloidal metals such as molybdenum, tungsten, magnesium, aluminum, nickel, bismuth, antimony, chromium, cobalt, zinc, cadmium, tin, or iron, sulfur, hydrogen sulfide, sulfur dioxide, hydrazine hydrate, ammonia, hydroxylamine, organic reducing agents, such as, sugars, pyrogallol, and the like. Most preferred is finely divided metal in the amount of from about 0.01 to 0.2 atoms of metal per mole of molybdenum trioxide present. It is also preferred that the promoter element be added in a non-oxidizing form.

On refluxing the aqueous suspension of molybdenum trioxide with the reducing agent, at least a part of the normally insoluble molybdenum trioxide is solubilized forming an intense deep blue coloration. It is hypothesized that this blue color which develops is the result of the reduction of molybdenum, at least in part, to a lower oxidation state in the oxidation-reduction reaction occurring between hexavalent molybdenum and the reducing metal. Although preferredly the molybdenum trioxide is pre-reduced before reaction with the antimony trioxide, beneficial results are also obtained by first reacting the molybdenum trioxide with antimony trioxide followed by reaction with the reducing agent, or by reacting the three components simultaneously. It is also contemplated to be within the scope of this invention to employ a combination of a lower oxide of molybdenum with a higher oxide of antimony, as for example antimony tetroxide or antimony pentoxide in preparation of the catalyst.

Preferredly, the metal promoter of the catalyst is subsequently added to the aqueous suspension of mixed oxides of antimony, molybdenum and the reducing metal, in the form of a non-oxidizing compound such as, for example, the metal oxide, hydrous metal oxide, the hydroxide, the halide, the acid, a salt of the acid, a salt of an organic acid, an organometallic compound and the like. Satisfactory results are also obtained, however, by adding the promoter element to the component mixture at any stage of the catalyst preparation.

A highly reproducible method for combining the components of the catalyst of this invention comprises refluxing an aqueous suspension of molybdenum trioxide and a finely divided metal for a period of about 1 to 3 hours at 100°C until the deep blue coloration characteristic of a lower oxidation state of molybdenum appears. Antimony trioxide is then added to the aqueous suspension of the reduced molybdenum oxide and the reducing metal and this mixture is again refluxed at 100°C for a period of about 1 to 5 hours. To this mixture is added the metal promoter in a form disclosed hereinabove, and the entire mixture is further refluxed for about 1 to 5 hours at the same temperature. The aqueous slurry is then evaporated to dryness, and final drying is accomplished by placing the catalyst in an oven at a temperature of about 120° to 130° C for a period of from about 2 to 24 hours.

The catalyst of this invention may be supported on a carrier material such as for example, silica, zirconia, calcium stabilized-zirconia, titanis, alumina, thoria, silicon carbide, clay, pumice, diatomaceous earth and the like, or it may be employed satisfactorily in an unsupported form. If a carrier is utilized it may be employed in amounts of up to 95 percent by weight of the total catalyst composition.

The catalyst system herein described is useful in the oxidation of olefins to corresponding oxygenated compounds, such as unsaturated aldehydes and acids, and in the ammoxidation of olefins to unsaturated nitriles. Nitriles and oxygenated compounds such as aldehydes and acids can be produced simultaneously using process conditions within the overlapping ranges for these reactions, as set forth in detail below. The relative proportions of each that are obtainable will depend on the catalyst and on the olefin employed. It is also contemplated to be within the scope of this invention, that with the catalyst system employed herein, the unsaturated aldehyde may be further oxidized in a second step to the corresponding unsaturated acid. The unsaturated aldehyde need not be isolated from the other reaction products and can be further oxidized to the unsaturated acid while remaining in the reaction mixture. The term "oxidation" as used in this specification and claims encompasses the oxidation to aldehydes and acids and to nitriles, all of which conversions require oxygen as a reactant.

Oxidation of Olefins to Aldehydes and Acids

The reactants used in the oxidation to obtain oxygenated compounds are oxygen and an olefin such as propylene or isobutylene, or their mixtures.

The olefins may be in admixture with paraffinic hydrocarbons, such as ethane, propane, butane and pentane, as for example, a propylene-propane mixture may constitute the feed. This makes it possible to use ordinary refinery streams without special preparation.

The temperature at which this oxidation is conducted may vary considerably depending upon the catalyst, the particular olefin being oxidized and the correlated conditions of the rate of throughput or contact time and the ratio of olefin to oxygen. In general, when operating at pressures near atmospheric, i.e., −10 to 100 p.s.i.g., temperatures in the range of 250° to 600°C may be advantageously employed. However, the process may be conducted at other pressures, and in the case where superatmospheric pressures, e.g., above 100 p.s.i.g. are employed somewhat lower temperatures are feasible. In the case where this process is employed to convert propylene to acrolein and acrylic acid, or isobutylene to methacrolein and methacrylic acid, a temperature range of from about 300° to 500°C has been found to be optimum at atmospheric pressure.

While pressures other than atmospheric may be employed it is generally preferred to operate at or near atmospheric pressure, since the reaction proceeds well at such pressures and the use of expensive high pressure equipment is avoided. Pressures of between atmospheric and 30 p.s.i.g. are most preferred.

The apparent contact time employed in the process is not critical and may be selected from a broad operable range which may vary from 0.1 to 50 seconds. The apparent contact time may be defined as the length of time in seconds which the unit volume of gas measured under the conditions of reaction is in contact with the apparent unit volume of the catalyst. It may be calculated, for example, from the apparent volume of the catalyst bed, the average temperature and pressure of the reactor, and the flow rates of the several components of the reaction mixture.

The optimum contact time will, of course, vary depending upon the olefin being treated, but in the case of propylene and isobutylene the preferred apparent contact time is 0.5 to 15 seconds.

A molar ratio of oxygen to olefin between about 0.5:1 to 10:1 generally gives the most satisfactory results. For the conversion of propylene to acrolein, and isobutylene to methacrolein and methacrylic acid, a preferred ratio of oxygen to olefin is from about 1:1 to about 5:1. The oxygen used in the process may be derived from any source; however, air is the least expensive source of oxygen, and is preferred.

The addition of water to the reaction mixture has a marked beneficial influence on the course of the reaction in that it improves the conversion and the yield of the desired product. Accordingly, we prefer to include water in the reaction mixture. Generally, a ratio of olefin to water in the reaction mixture of from 1:0.5 to 1:10 will give very satisfactory results, and a ratio of from 1:1 to 1:6 has been found to be optimum when converting propylene to acrolein and acrylic acid, and isobutylene to methacrolein and methacrylic acid. The water, of course, will be in the vapor phase during the reaction.

Inert diluents such as nitrogen and carbon dioxide may be present in the reaction mixture.

Oxidation of Olefins to Nitriles

The reactants used are the same as those employed in the production of aldehydes and acids above, plus ammonia. Any of the olefins described can be used.

In its preferred aspect, the process comprises contacting a mixture comprising propylene or isobutylene, ammonia and oxygen with the catalyst at an elevated temperature and at atmospheric or near atmospheric pressure.

Any source of oxygen may be employed in this process. For economic reasons, however, it is preferred that air be employed as the source of oxygen. From a purely technical viewpoint, relatively pure molecular oxygen will give equivalent results. The molar ratio of oxygen to the olefin in the feed to the reaction vessel should be in the range of 0.5:1 to 10:1 and a ratio of about 1:1 to 5:1 is preferred.

Low molecular weight saturated hydrocarbons do not appear to influence the reaction to an appreciable degree, and these materials can be present. Consequently, the addition of saturated hydrocarbons to the feed to the reaction is contemplated within the scope of this invention. Similarly diluents such as nitrogen and the oxides of carbon may be present in the reaction mixture without deleterous effect.

The molar ratio of ammonia to olefin in the feed to the reaction may vary between about 0.05:1 to 5:1. There is no real upper limit for the ammonia-olefin ratio, but there is generally no reason to exceed the 5:1 ratio. At ammonia-olefin ratios appreciably less than the stoichiometric ratio of 1:1, various amounts of oxygenated derivates of the olefin will be formed.

Significant amounts of unsaturated aldehydes and even unsaturated acids as well as nitriles will be obtained at ammonia-olefin ratios substantially below 1:1, i.e., in the range of 0.15:1 to 0.75:1, particularly in the case of higher olefins such as isobutylene. Outside the upper limit of this range only insignificant amounts of aldehydes and acids will be produced, and only small amounts of nitriles will be produced at ammonia-olefin ratios below the lower limit of this range. It is generally possible to recycle any unreacted olefin and unconverted ammonia.

We have found that in many cases water in the mixture fed to the reaction vessel improves the selectivity of the reaction and yield of nitrile. However, reactions not including water in the feed are not to be excluded from this invention, inasmuch as water is formed in the course of the reaction. Sometimes it is desirable to add some water to the reaction mixture, and in general, molar ratios of added water to olefin, when water is added, on the order of 1:1 to 4:1 are particularly desirable. However higher ratios may be employed, i.e., ratios of up to about 10:1 are feasible.

The reaction is carried out at a temperature within the range from about 250° to about 600°C. The preferred temperature range is from about 350° to 500°C.

The pressure at which the reaction is conducted is not critical, and the reaction should be carried out at about atmospheric pressure or pressures up to about 5 atmospheres. In general, high pressures, i.e. about 15 atmospheres, are not suitable, since higher pressures tend to favor the formation of undesirable by-products.

The apparent contact time is an important variable, and contact time in the range of from 0.1 to about 50 seconds may be employed. The optimum contact time will, of course, vary, depending upon the olefin being treated, but in general, a contact time of from 1 to 15 seconds is preferred.

In general, any apparatus of the type suitable for carrying out oxidation reactions in the vapor phase may be employed in the execution of this process. The processes may be conducted either continuously or intermittently. The catalyst bed may be a fixed bed employing a large particulate or pelleted catalyst, or in the alternative, a so-called "fluidized" bed of catalyst may be employed.

The reactor may be brought to the reaction temperature before or after the introduction of the reaction feed mixture. However, in a large scale operation, it is preferred to carry out the process in a continuous manner, and in such a system the recirculation of the unreacted olefin is contemplated. Periodic regeneration or reactivation of the catalyst is also contemplated, and this may be accomplished, for example, by contacting the catalyst with air at an elevated temperature.

The products of the reaction may be recovered by any of the methods known to those skilled in the art. One such method involves scrubbing the effluent gases from the reactor with cold water or an appropriate solvent to remove the products of the reaction. In the recovery of nitrile products it may be desirable to employ acidified water to absorb the products reaction and neutralize unconverted ammonia. The ultimate recovery of the products may be accomplished by conventional means, such as by distillation or solvent extraction. The efficiency of the scrubbing operation may be improved when water is employed as the scrubbing agent by adding a suitable wetting agent to the water. Where molecular oxygen is employed as the oxidizing agent in this process, the resulting product mixture remaining after the removal of the aldehydes, acids and nitriles may be treated to remove carbon dioxide with the remainder of the mixture containing the unreacted olefin and oxygen being recycled through the reactor. In the case where air is employed as the oxidizing agent in lieu of molecular oxygen, the residual product after separation of the nitriles and other carbonyl products may be scrubbed with a non-polar solvent, e.g., a hydrocarbon fraction, in order to recover unreacted olefin, and in this case the remaining gases may be discarded. The addition of a suitable inhibitor to prevent polymerization of the unsaturated products during the recovery steps is also contemplated.

The following examples are representative of the process conditions and catalyst compositions that are suitable for the process of this invention, however, the scope of the invention is not to be limited by these examples.

In the examples, the activity of the catalysts was determined using a fixed-bed microreactor composed of a feed induction system, a molten salt bath furnace, a scrubber and a vapor phase chromatograph. The reactor was constructed from a 5 inches length of pipe having a ⅜ inch I.D., and a catalyst capacity of approximately 4 cc of catalyst.

The catalyst employed had a particle size of 20–32 mesh. The reaction product obtained from the oxidation reaction was absorbed in a water scrubber and the ammoxidation product was absorbed in a water-hydrochloric acid scrubber solution. An aliquot of the scrubber liquid was subsequently injected into a Hewlett and Packard gas chromatograph Model No. 5750 for analysis. The chromatograph contained a Porapak-Q column, 2 meters in length and ⅛ inch in diameter.

The column was maintained at a temperature of 180°C for the analysis of acrolein, methacrolein, acrylonitrile, methacrylonitrile and acetic acid, and at 230°C for the analysis of acrylic acid and methacrylic acid. The unabsorbed gaseous product, consisting essentially of carbon monoxide, carbon dioxide, oxygen, nitrogen and unreacted hydrocarbon, was analyzed by means of a Fisher Gas Partitioner. Hydrogen cyanide and ammonia when present were determined by titration.

The reaction conditions employed and the conversions obtained utilizing the various hydrocarbon feeds and catalyst compositions described in the invention are summarized in Tables 1 to 5. In these experiments, the results are reported as the mole percent per pass conversion to the desired product which is defined as:

$$\frac{\text{Moles of desired product recovered}}{\text{Moles of olefin in the feed}} \times 100$$

and selectivity on a molar basis is defined as:

$$\frac{\text{Moles of desired product recovered}}{\text{Moles of olefin converted}} \times 100$$

The catalysts employed in Examples 1 to 40 (Tables 2 to 5) were prepared according to the following procedures:

EXAMPLE 1

64.8 Grams of molybdenum trioxide ($MoO_3$) (0.45 gram atoms of Mo) was slurried in water and heated at 100°C for one hour. 43.7 Grams of antimony trioxide ($Sb_2O_3$) (0.3 gram atoms of Sb) was added to the aqueous slurry and refluxing was continued for five hours at 110°C. This was then stirred constantly at room temperature for 16 hours. The bulk of the slurry was then slowly evaporated to dryness, and the solid was then dried at 130°C for 40 hours.

EXAMPLE 2

64.8 Grams of molybdenum trioxide ($MoO_3$) (0.45 gram atoms of Mo) were reacted with 0.864 grams of molybdenum metal powder (0.009 gram atoms of Mo) in about 300 cc of water. The aqueous slurry was refluxed for about one hour with constant stirring. The color of the slurry on completion of the reaction was blue. To this slurry was added 43.7 grams of antimony trioxide ($Sb_2O_3$) (0.3 gram atoms of Sb), and stirring at reflux temperatures was continued at least for one additional hour. The color of the slurry was dark green.

The promoted catalysts were prepared by adding the promoter element to the slurry of Example 2 in the form of the compound and the amount of the compound indicated in Table I. The slurry containing the added promoter element was refluxed for 3 more hours with continual stirring, was then placed in a large beaker and was slowly evaporated to dryness over a hot plate. The solid was finally dried in an oven at 130°C for about 24 hours.

to methacrolein with the promoted, reduced, antimony-molybdenum catalysts as compared with the unpromoted catalysts for this same reaction. The data in this Table also show the effect of varying the concentration of the promoter, the use of more than one promoter in Table I

| Example | Reducing Element in place of Mo° | (grams) | Promoter Element | Grams of Compound Used |
|---|---|---|---|---|
| 3 | $Al_{0.06}$ | 0.243 | — | |
| 4 | $Ni_{0.06}$ | 0.528 | — | |
| 5 | $S_{0.06}$ | 0.289 | — | |
| 6 | $W_{0.06}$ | 1.655 | | |
| 7 | $Mo_{0.06}$ | 0.864 | $Bi_{0.01}$ | 0.727 $Bi(NO_3)_3.5H_2O$ + $HNO_3$ |
| 8 | " | " | $Bi_{0.1}$ | 6.61 $Bi(C_6H_5)_3$ |
| 9 | " | " | $Bi_{0.1}$ | 7.27 $Bi(NO_3)_3.5H_2O$ |
| 10 | " | " | $P_{0.01}$ | 0.173 $H_3PO_4$ (85% soln.) |
| 11 | " | " | $P_{0.1}$ | 1.73 $H_3PO_4$ (85% soln.) |
| 12 | " | " | $P_{0.25}$ | 4.325 " |
| 13 | " | " | $P_{0.5}$ | 8.647 " |
| 14 | " | " | $P_{1.0}$ | 17.299 " |
| 15 | " | " | $B_{0.01}$ | 0.093 $H_3BO_3$ |
| 16 | " | " | $Te_{0.01}$ | 0.404 $TeCl_4$ |
| 17 | " | " | $Te_{0.1}$ | 4.041 $TeCl_4$ |
| 18 | $W_{0.06}$ | 1.655 | $Te_{0.1}$ | 4.041 $TeCl_4$ |
| 19 | $W_{0.2}$ | 5.52 | $Te_{0.1}$ | 4.041 $TeCl_4$ |
| 20 | $Mo_{0.06}$ | 0.864 | $W_{0.1}$ | 3.75 $H_2WO_4$ |
| 21 | " | " | $Mn_{0.1}$ | 1.726 $MnCO_3$ |
| 22 | " | " | $Ni_{0.1}$ | 1.781 $NiCO_3$ |
| 23 | " | " | $Cu_{0.1}$ | 2.02 $CuCl_2$ |
| 24 | " | " | $Pb_{0.1}$ | 5.69 $Pb(C_2H_3O_2)_2.3H_2O$ |
| 25 | " | " | $Re_{0.1}$ | 4.02 $NH_4ReO_4$ |
| 26 | " | " | $Sn_{0.1}$ | 3.38 $SnCl_2.2H_2O$ |
| 27 | " | " | $Te_{0.1},Sn_{0.1}$ | 3.38 $SnCl_2.2H_2O$ 4.04 $TeCl_4$ |
| 28 | " | " | $Cr_{0.1}$ | 1.50 $CrO_3$ |
| 29 | " | " | $Ni_{0.1}$ | 1.78 $NiCO_3$ |
| 30 | " | " | $Ti_{0.1}$ | 1.20 $TiO_2$ |
| 31 | " | " | $W_{0.1}$ | 3.75 $H_2WO_4$ |
| 32 | " | " | $Fe_{0.05}$ | 2.02 $FeCl_3$ |
| 33 | " | " | $Te_{0.1}Fe_{0.05}$ | 4.04 $TeCl_4$, 2.02 $FeCl_3$ |
| 34 | " | " | $U_1$ | 137 g heat treated $USb_3O_{10}$ |
| 35 | " | " | $P_{0.1}$ | 1.73 $H_3PO_4$ (85% soln.) |
| 36 | " | " | $Te_{0.1}$ | 4.041 $TeCl_4$ |
| 37 | " | " | — | same as in Example 2 |
| 38 | " | " | $Te_{0.1}$ | 4.041 $TeCl_4$ |
| 39 | " | " | — | same as in Example 2 |
| 40 | " | " | $P_{0.1}$ | 1.73g $H_3PO_4$ (85% soln.) |

The effectiveness of the catalyst of this invention for the conversion of olefins to the corresponding unsaturated aldehydes, acids and nitriles is demonstrated by the conversion of isobutylene to methacrolein, methacrylic acid and methacrylonitrile, and propylene to acrolein, and acrylic acid shown in the examples in Tables 2 to 5. The examples in Table 2 illustrate the improvement obtained in the conversion of isobutylene the catalyst, and the effect of varying the reaction conditions such as the inclusion of water in the feed. The examples given in Tables 3 to 5 show the effect of these catalysts for the oxidation of other feeds such as propylene and methacrolein to acrolein and methacrylic acid, respectively, and the ammoxidation of isobutylene to methacrylonitrile.

TABLE II

Oxidation of Isobutylene to Methacrolein
Reaction Conditions
Molar Feed Ratio, $IC_4^=$/air 1/20
Contact Time 3 seconds
Temperature, °C = 371

| Example | Catalyst | Mole Percent Conversion to: Methacrolein | Mole Percent Conversion to: Methacrylic Acid | Mole Percent Selectivity to Methacrolein |
|---|---|---|---|---|
| 1 | $Sb_2Mo_3O_x$ | 35.6 | — | 57 |
| 2 | $Sb_2Mo_3O_x$ + $Mo_{0.06}$° 37.9 | 3.0 | 61 | |
| 3 | $Sb_2Mo_3O_x$ + $Al_{0.06}$° | 44.2 | 1.2 | 54 |
| 4 | " + $Ni_{0.06}$° | 43.9 | 1.0 | 59 |
| 5 | " + $S_{0.06}$° | 42.9 | 2.9 | 65 |
| 6 | " + $W_{0.06}$ | 37.6 | 4.4 | 42 |
| 7 | $Bi_{0.01}[Sb_2Mo_3O_x + Mo_{0.06}°]$ ($HNO_3$ was used during the preparation) | tr | tr | — |
| 8 | $Bi_{0.1}[Sb_2MoO_3O_x + Mo_{0.06}°]$ | 44.2 | tr | 62 |
| 9 | $Bi_{0.1}[Sb_2Mo_3O_x + Mo_{0.06}°]$ (Nitrate free) | 53.4 | 1.9 | 63 |
| 10 | $P_{0.01}[Sb_2Mo_3O_x + Mo_{0.06}°]$ | 48.4 | 1.8 | 57 |
| 11 | $P_{0.1}[Sb_2Mo_3O_x + Mo_{0.06}°]$ | 30.3 | 12.1 | 42 |
| 12 | $P_{0.25}$ " | 17.6 | tr | 68 |
| 13 | $P_{0.5}$ " | 19.9 | 0.5 | 50 |
| 14 | $P_{1.0}$ " | 6.8 | 0.3 | 30 |
| 15 | $B_{0.01}$ " | 57.2 | 2.2 | 60 |

TABLE II-continued

Oxidation of Isobutylene to Methacrolein
Reaction Conditions
Molar Feed Ratio, $IC_4^=$/air 1/20
Contact Time 3 seconds
Temperature, °C = 371

| Example | Catalyst | Mole Percent Conversion to: Methacrolein | Mole Percent Conversion to: Methacrylic Acid | Mole Percent Selectivity to Methacrolein |
|---|---|---|---|---|
| 16 | $Te_{0.01}$ " | 63.5 | — | 80 |
| 17 | $Te_{0.1}$ " | 71.7 | — | 77 |
| 18 | $Te_{0.1}[Sb_2Mo_3O_x + W_{0.06}°]$ | 62.2 | 7.2 | 74 |
| 19 | $Te_{0.1}[Sb_2Mo_3O_x + W_{0.2}°]$ | 49.1 | 5.1 | 55 |
| 20 | $W_{0.1}[Sb_2Mo_3O_x + Mo_{0.06}°]$ | 58.2 | — | 60 |
| 21 | $Mn_{0.1}$ " | 56.5 | 0.3 | 74 |
| 22 | $Ni_{0.1}$ " | 56.5 | 0.7 | 70 |
| 23 | $Cu_{0.1}$ " | 56.4 | — | 70 |
| 24 | $Pb_{0.1}$ " | 55.5 | 1.2 | 69 |
| 25 | $Re_{0.1}$ " | 46.1 | — | 48 |
| 26 | $Sn_{0.1}$ " | 42.4 | 6.4 | 53 |
| 27 | $Te_{0.1}Sn_{0.1}$ " | 77.9 | — | 85 |
| 28 | $Cr_{0.1}$ " | 41.2 | tr | 52 |
| *29 | $Ni_{0.1}[Sb_2Mo_3O_x + Mo_{0.06}°]$ | 62.5 | 1.3 | 73 |
| *30 | $Ti_{0.1}$ " | 61.2 | 3.9 | 70 |
| *31 | $W_{0.1}$ " | 60.6 | 3.8 | 70 |
| 32 | $Fe_{0.5}$ " | 41.4 | tr | 46 |
| 33 | $Te_{0.1}Fe_{0.05}$ " | 60.1 | | |
| 34 | $U_1[Sb_{4.67}Mo_{2.5} + Mo_{0.05}]$ | 55.0 | 4.3 | 59 |

*Molar Feed ratio, $IC_4^=$/air/$H_2O$ = 1/11/4
Reaction Temp.,°C = 399

Table III

Oxidation of Propylene to Acrolein
Reaction Conditions
Molar Feed Ratio, $C_3^=$/air = 1/20

| Example | Catalyst | Reaction Temp. (°C) | C.T. (Secs) | Mole Percent Conversion to: Acrolein | Mole Percent Conversion to: Acrylic Acid | Mole Percent Selectivity to Acrolein |
|---|---|---|---|---|---|---|
| 35 | $P_{0.1}[Sb_2Mo_3O_x + Mo_{0.06}°]$ | 400 | 3.0 | 20.7 | — | 66 |
| 36 | $Te_{0.1}$ " | 450 | 5.0 | 42.5 | 7.9 | 84 |

Table IV

Ammoxidation of Isobutylene to Methacrylonitrile
Reaction Conditions
Molar Feed Ratio, $IC_4^=$/$NH_3$/air = 1/1.5/20
Contact time = 3 seconds
Temperature, °C = 399

| Example | Catalyst | Mole Percent Conversion to: Methacrylonitrile | Mole Percent Conversion to: Acrolein & Methacrolein | Mole Percent Selectivity to Methacrylonitrile |
|---|---|---|---|---|
| 37 | $[Sb_2Mo_3O_x + Mo_{0.06}°]$ | 42.5 | 1.9 | 43 |
| 38 | $Te_{0.1}[Sb_2Mo_3O_x + Mo_{0.06}°]$ | 71.1 | 3.5 | 73 |

Table V

Oxidation of Methacrolein to Methacrylic Acid
Reaction Conditions
Molar Feed Ratio, Methacrolein/Air/$H_2O$ = 1/6/5
Contact Time, sec. = 1.0
Temperature, °C = 400

| Example | Catalyst | Mole Percent conversion to: Methacrylic Acid | Mole Selectivity to Methacrylic Acid |
|---|---|---|---|
| 39 | $[Sb_2Mo_3O_x + Mo_{0.06}°]$ | 11.9 | 57 |
| 40 | $P_{0.1}[Sb_2Mo_3O_x + Mo_{0.06}°]$ | 25.6 | 53 |

We claim:

1. A process for the oxidation of propylene and isobutylene to form the corresponding unsaturated aldehydes and unsaturated acids comprising contacting in the vapor phase at a temperature within the range of from about 250° to about 600°C. a mixture of a molecular oxygen-containing gas and either propylene or isobutylene, or mixtures thereof, in a molar ratio of oxygen to olefin within the range from about 0.5 to 10, in the presence of a promoted, reduced, antimony oxide-molybdenum oxide-containing catalyst wherein the catalyst is prepared by combining the following components in any order:

a. an aqueous slurry of molybdenum trioxide;
b. a reducing agent selected from the group consisting of finely divided metal, sulfur, sulfur dioxide, hydrogen sulfide, hydrazine hydrate, ammonia, hydroxylamine and an organic reducing agent capable of reducing at least some of the molybdenum to a valence state below +6 in a ratio of from about 0.0001 to 0.2 moles of the reducing agent per mole of molybdenum;

c. antimony oxide in a ratio of from about 0.1 to 9 moles of antimony oxide per mole of molybdenum; and
d. at least one promoter element in the form of a non-oxidizing compound selected from the group consisting of tellurium, tungsten, titanium, manganese, nickel, iron, copper, lead, rhenium, bismuth, tin, uranium, chromium, phosphorus and boron, said promoter element being added in a ratio of from about 0.0001 to 1.0 moles of promoter element per mole of molybdenum.

2. The process in claim 1 wherein the finely divided metal in component (b) in the catalyst preparation is selected from the group consisting of molybdenum, tungsten, aluminum and nickel.

3. The process in claim 2 wherein the catalyst components are combined in the following order:
a. molybdenum trioxide is reacted with the reducing agent;
b. antimony trioxide is added to the reaction mixture of (a); and
c. the promoter element in the form of a non-oxidizing compound is subsequently added to the reaction mixture of (b).

* * * * *